(12) United States Patent
Dewey

(10) Patent No.: US 8,216,240 B2
(45) Date of Patent: Jul. 10, 2012

(54) CAM BASED REDUCTION INSTRUMENT

(75) Inventor: Jonathan Dewey, Memphis, TN (US)

(73) Assignee: Warsaw Orthopedic, Warsaw, IN (US)

(*) Notice: Subject to any disclaimer, the term of this patent is extended or adjusted under 35 U.S.C. 154(b) by 1305 days.

(21) Appl. No.: 11/409,774

(22) Filed: Apr. 24, 2006

(65) Prior Publication Data
US 2007/0270868 A1 Nov. 22, 2007

(51) Int. Cl.
A61B 17/70 (2006.01)
A61F 2/46 (2006.01)

(52) U.S. Cl. ........................ 606/86 A; 606/86 R; 606/99

(58) Field of Classification Search ................. 606/86 A, 606/86 B, 86 R, 99–100
See application file for complete search history.

(56) References Cited

U.S. PATENT DOCUMENTS

| | | | |
|---|---|---|---|
| 5,437,670 A | 8/1995 | Sherman et al. | |
| 5,454,811 A | 10/1995 | Huebner | |
| 5,611,800 A | 3/1997 | Davis et al. | |
| 5,624,441 A | 4/1997 | Sherman et al. | |
| 5,688,275 A * | 11/1997 | Koros et al. | 606/264 |
| 6,036,692 A * | 3/2000 | Burel et al. | 606/86 A |
| 6,203,543 B1 | 3/2001 | Glossop | |
| 6,565,565 B1 | 5/2003 | Yuan | |
| 6,945,975 B2 | 9/2005 | Dalton | |
| 6,979,334 B2 | 12/2005 | Dalton | |
| 2002/0095153 A1 * | 7/2002 | Jones et al. | 606/61 |
| 2002/0120272 A1 | 8/2002 | Yuan et al. | |
| 2002/0161368 A1 * | 10/2002 | Foley et al. | 606/61 |
| 2003/0125742 A1 | 7/2003 | Yuan et al. | |
| 2004/0030337 A1 | 2/2004 | Alleyne et al. | |
| 2004/0138662 A1 * | 7/2004 | Landry et al. | 606/61 |
| 2004/0153068 A1 | 8/2004 | Janowski et al. | |
| 2005/0033299 A1 * | 2/2005 | Shluzas | 606/61 |
| 2005/0142515 A1 * | 6/2005 | Levy et al. | 433/114 |
| 2005/0182416 A1 * | 8/2005 | Lim et al. | 606/90 |
| 2005/0228385 A1 | 10/2005 | Iott et al. | |
| 2005/0252060 A1 * | 11/2005 | Gonzalez | 42/90 |
| 2005/0267474 A1 | 12/2005 | Dalton et al. | |
| 2005/0288671 A1 | 12/2005 | Yuan et al. | |
| 2006/0004357 A1 | 1/2006 | Lee et al. | |
| 2006/0004359 A1 | 1/2006 | Kramer et al. | |
| 2006/0004360 A1 | 1/2006 | Kramer et al. | |
| 2006/0015104 A1 | 1/2006 | Dalton | |
| 2007/0161998 A1 * | 7/2007 | Whipple | 606/61 |

* cited by examiner

Primary Examiner — Eduardo C Robert
Assistant Examiner — Julianna N Harvey

(57) ABSTRACT

A rod reduction instrument for urging a rod into an implant having a stabilization member receiving area is provided. The rod reduction instrument includes an arm with a first end connected with the implant. A ram lever is provided that is pivotally connected to the arm. The ram lever has a cam surface for contact with the rod. Pivotal movement of the ram lever reduces the rod into the implant stabilization member receiving area.

14 Claims, 5 Drawing Sheets

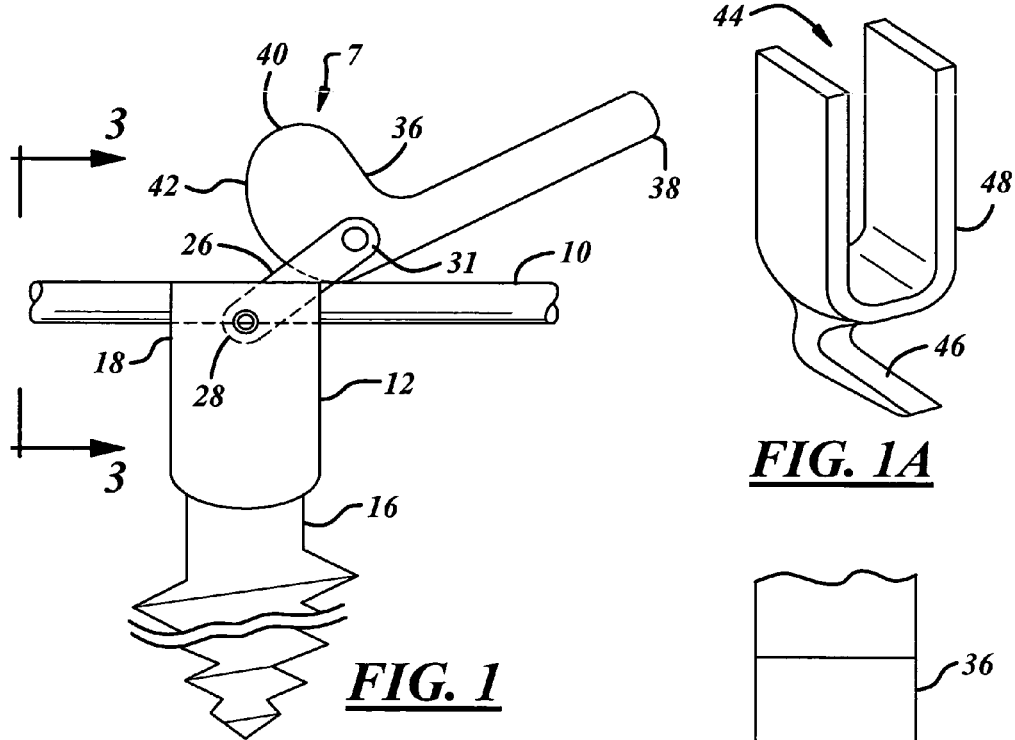
FIG. 1
FIG. 1A
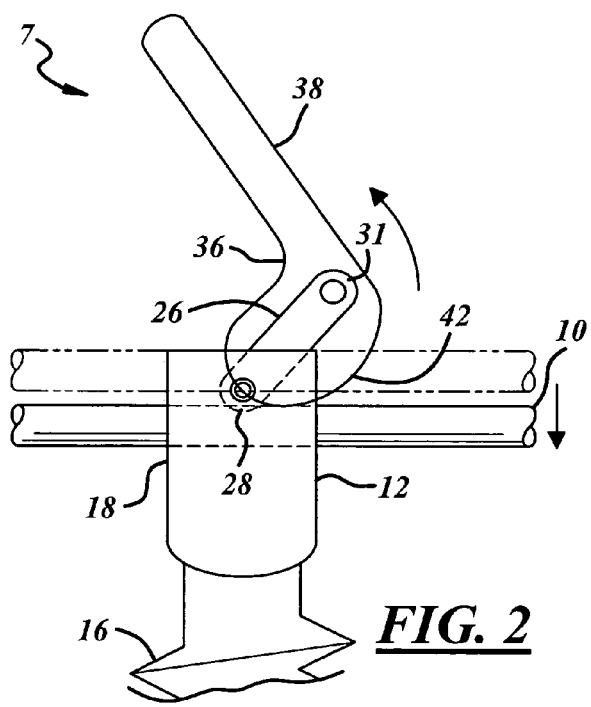
FIG. 2
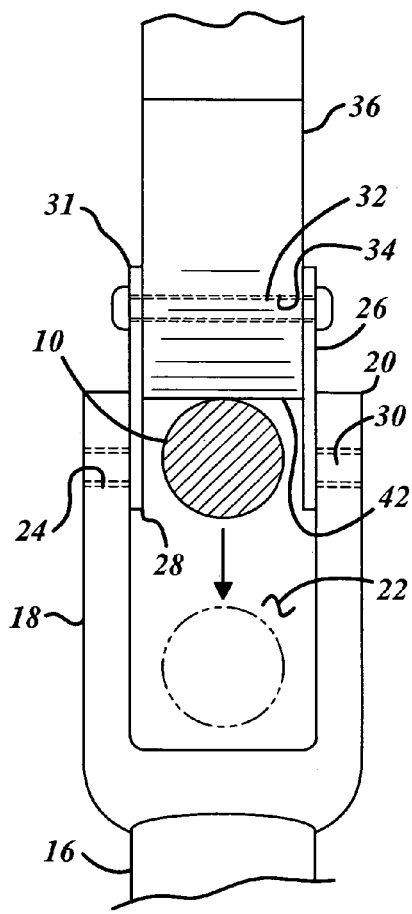
FIG. 3

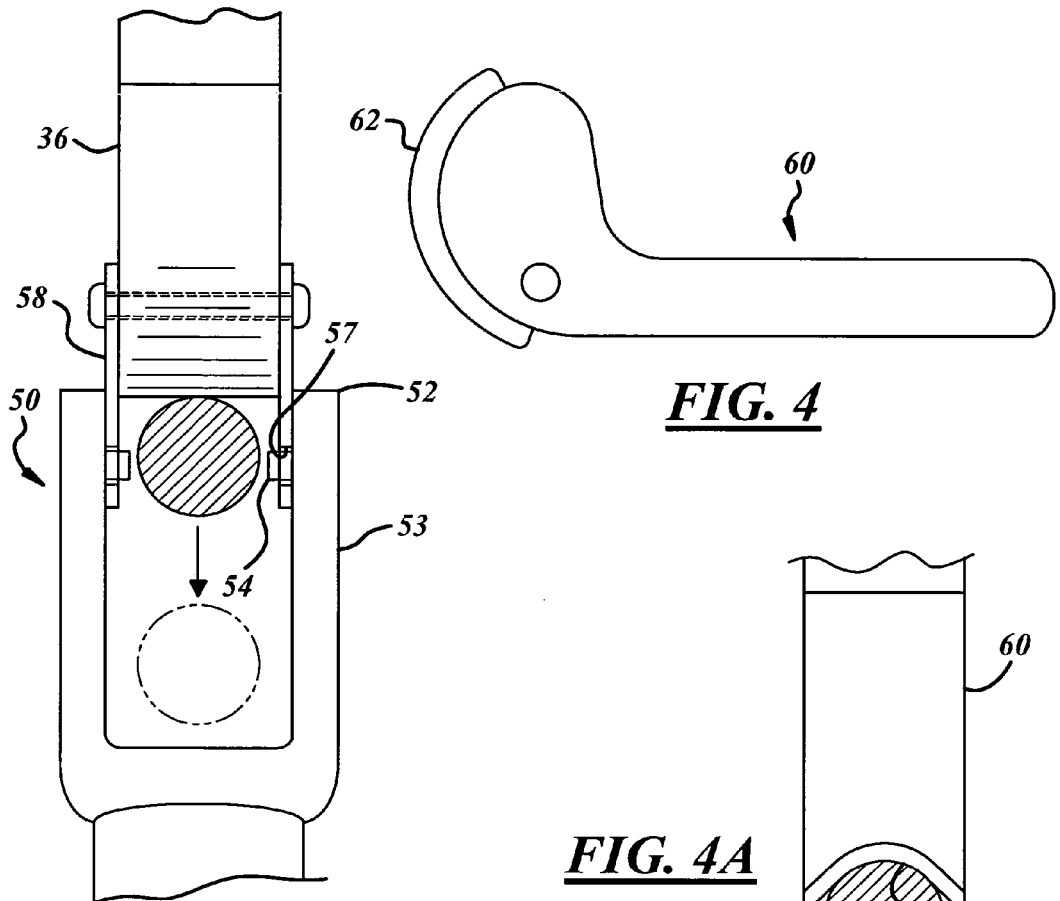
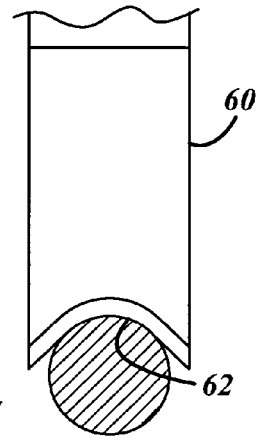
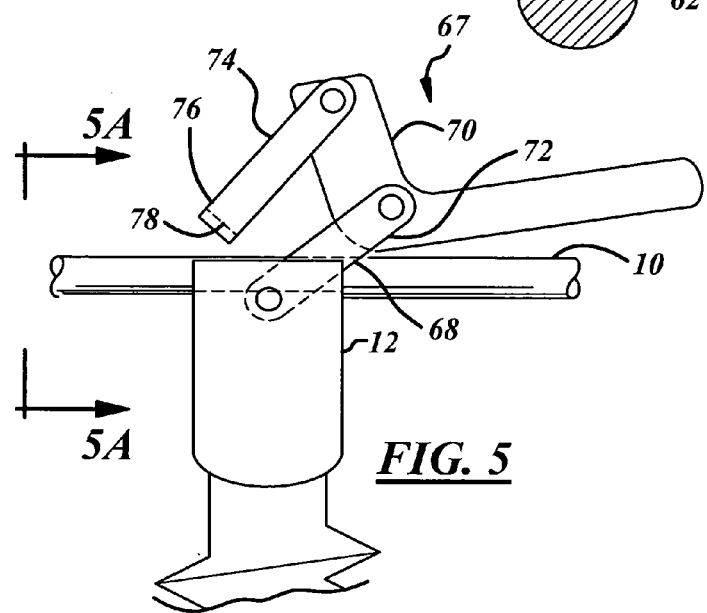

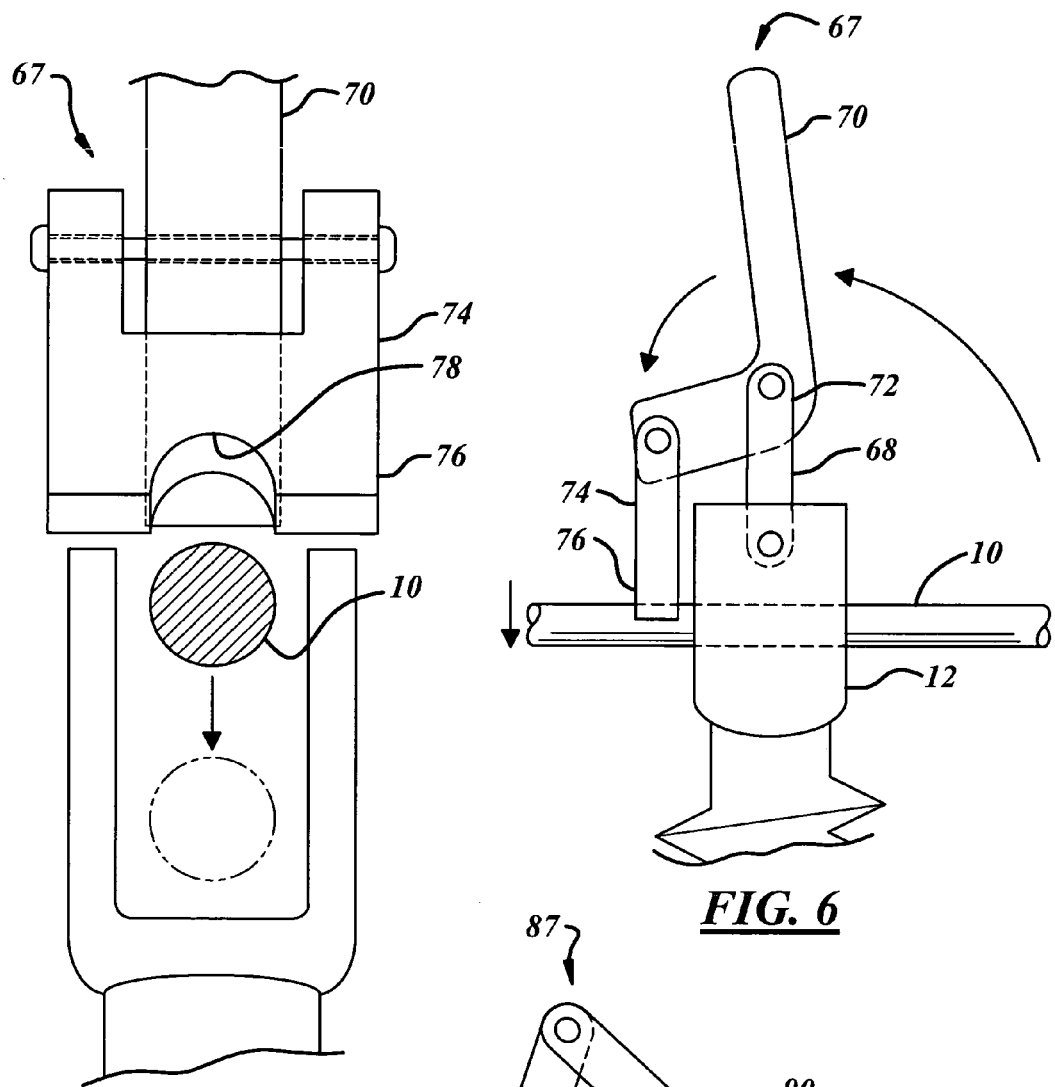
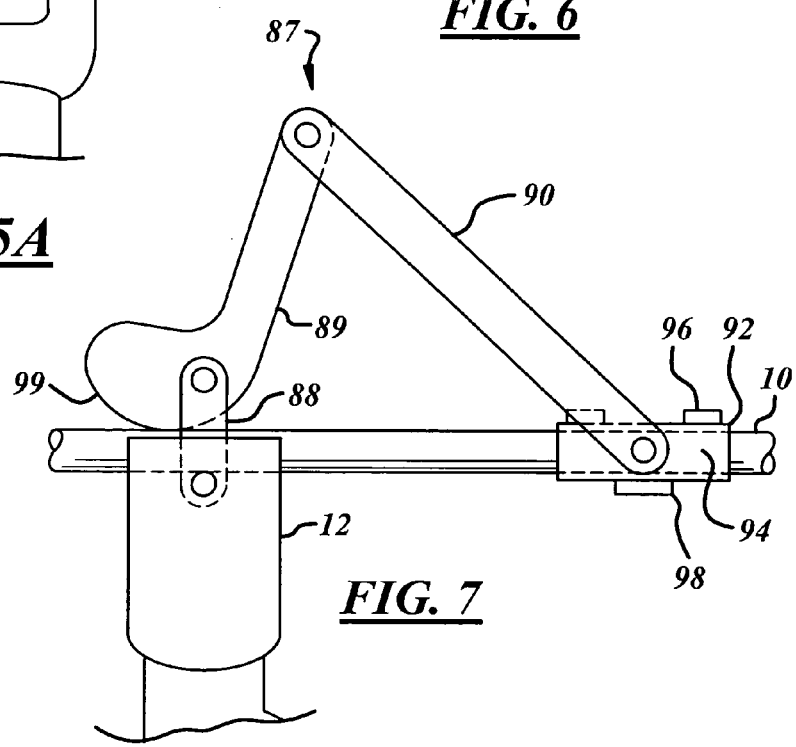
*FIG. 5A*
*FIG. 6*
*FIG. 7*

CAM BASED REDUCTION INSTRUMENT

FIELD OF THE INVENTION

The present invention relates to reducing instruments used for reducing stabilization members into medical implants.

BACKGROUND OF THE INVENTION

Spinal surgeons often treat spinal disorders with spinal fusion augmented with elongated spinal rods connected to the spine with implants such as pedicle screws or bone hooks. Such "rod assemblies" generally comprise one or two spinal rods and a plurality of screws inserted through the pedicles and into their respective vertebral bodies or hooks connected adjacent thereto. The implants are provided with U-shaped heads that can be capped to couple the elongate rod to the implants. During the surgical procedure to couple the rod to the implants, it is often necessary to use an instrument to push or "reduce" the rod onto the implants heads. An instrument and method of use thereof to reduce a rod into an implant is described in U.S. Pat. No. 6,036,692 Burel et al. commonly assigned. It is desirable to provide an alternative to the instrument described in Burel et al. and to provide such an instrument that offers the surgeon a mechanical advantage in the reduction procedure.

SUMMARY OF THE INVENTION

To make manifest the above noted and other manifold desires a revelation of the present invention is brought forth. The present invention provides an instrument for reducing a rod into a head of an implant. The instrument includes an arm with a first end connected with the implant. A ram lever is provided. The ram lever is pivotally connected to the arm and has a cam surface for contact with a rod. Pivotal movement of the ram lever reduces the rod into a stabilization member receiving area of the implant.

Other features of the invention will become more apparent to those skilled in the art as the invention is further revealed in the accompanying drawings and Detailed Description of the Invention.

BRIEF DESCRIPTION OF THE DRAWINGS

FIG. 1 is a side elevation view of a preferred embodiment rod reduction instrument of the present invention.

FIG. 1A is a perspective view of a bone hook implant that can have a rod reduced therein using a rod reduction instrument of the present invention.

FIG. 2 is a view similar to that of FIG. 1 illustrating operation of the rod reduction instrument shown in FIG. 1.

FIG. 3 view of the rod reduction instrument of the present invention taken along line 3-3 of FIG. 1.

FIG. 3A is a view similar to that of FIG. 3 illustrating an alternative preferred embodiment arm of the rod reduction instrument shown in FIG. 3.

FIG. 4 is a side elevation view of an alternative preferred embodiment ram lever of the rod reduction instrument shown in FIG. 1.

FIG. 4A is a partial front elevation view of the ram lever shown in FIG. 4.

FIG. 5 is a side elevation view of an alternate preferred embodiment rod reduction instrument of the present invention.

FIG. 5A is a view of the rod reduction instrument shown in FIG. 5 taken along line 5A-5A of FIG. 5.

FIG. 6 is a view similar to that of FIG. 5 illustrating operation of the rod reduction instrument shown in FIG. 5.

FIG. 7 is a side elevation view of another alternative preferred embodiment rod reduction instrument of the present invention.

DETAILED DESCRIPTION OF THE INVENTION

Figure 8:
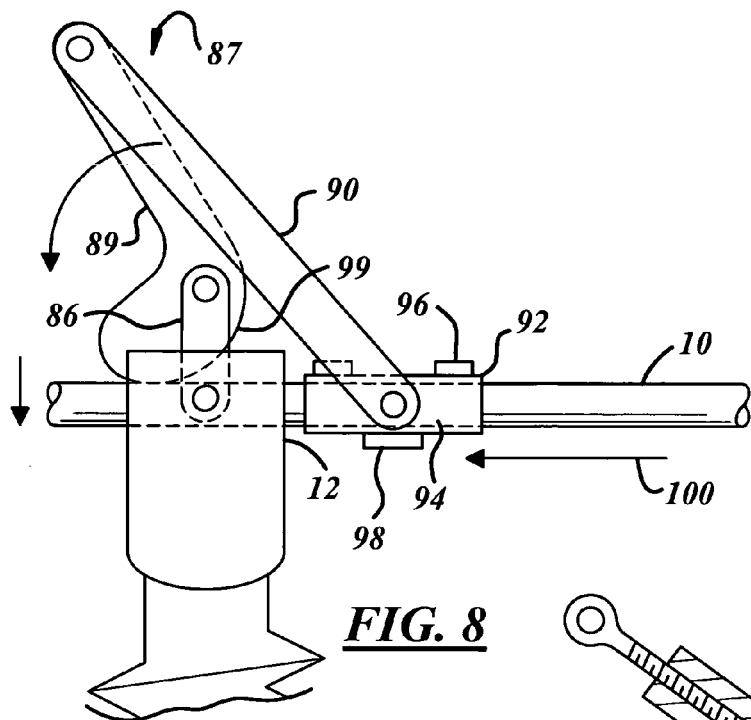
FIG. 8 is a view similar to that of FIG. 7 illustrating operation of the rod reduction instrument shown in FIG. 7.

Referring to FIGS. 1, 2 and 3, a rod reduction instrument 7 for urging an elongated rod 10 into a medical screw implant 12 is presented. The screw 12 has a threaded shank 16 with a connected head 18. The head 18 has two posts 20. A stabilization member receiving area 22 juxtaposes the posts 20. Each post 20 features a generally transverse cavity provided by an aperture 24. In certain spinal surgery procedures, a series of screws 12 are inserted into the vertebrate pedicle of the patient's spine. These medical screws are often referred to as pedicle screws. The screws 12 are connected with an elongated rod 10 to maintain their position and alignment. Often the rod 10 will have to be pushed into the stabilization member receiving area 22. The above noted process is often referred to as reducing the rod into the screw.

The instrument 7 includes two parallel spaced arms 26. Each arm 26 has a first end 28 connected with a respective post 20. In the embodiment of FIG. 1, the arm 26 has a protrusion 30 (FIG. 3) that fits within the aperture 24. A second end 31 of the arm is connected with a shaft 32. The shaft 32 extends through a cross bore 34 of a ram lever 36 thereby providing a pivotal connection between the ram lever 36 and the arms 26. In another embodiment (not shown), the arms can be connected with the implant head posts along the outboard side of the posts. The ram lever 36 has a handle 38 generally opposite a cam end 40. The cam end 40 provides a cam surface 42.

To reduce the rod 10 into the screw 12 the arms 26 are positioned to place the protrusions 30 into the apertures 24. To facilitate placement, the arms 26 can be flexed inwardly. The cam surface 42 is engaged with the rod 10. As shown in FIG. 2, an upward (counter clockwise) pull on the handle 38 causes the cam surface 42 to urge the rod 10 and screw 12 together reducing the rod 10 into the stabilization member receiving area 22. A cap (not shown) can then be connected with the posts 20 for retaining the rod 10 in its appropriate position.

Referring to FIG. 1A, the above noted instrument 7 can be utilized to reduce a rod into a lamina or bone hook 44. The bone hook 44 has a body 46 connected with a head 48 is a substantially similar to the head 18 of the screw 16.

Referring to FIG. 3A, an implant screw 50 is provided being substantially similar to the screw 12. The screw 50 has a head 52 with posts 53 having protrusions 54. The protrusions 54 are affixed via apertures 57 featured within the arms 58. The arms 58 are pivotally connected with the ram lever 36.

FIGS. 4 and 4A provide an alternative embodiment ram lever 60 that can be utilized with the instrument 7. The ram lever 60 has a polymeric wear material providing a cam surface 62. The wear material helps to prevent inadvertent damage to the screw 12 by aiding the prevention of the ram lever 60 sliding on the rod 10. As best illustrated in FIG. 4A the cam surface 62 is concave providing a contour approximating that of the rod.

FIGS. 5, 5A, and 6 present in alternative preferred embodiment rod reduction instrument 67. The instrument 67 has arms 68 (only one shown) substantially similar to the arms 26 or 58. A ram lever 70 is pivotally connected with a second end 72 of the arms 68. Pivotally connected with the ram lever 70 is a cam lever 74. An end 76 of the cam lever provides a cam surface 78. As the ram lever 70 is pulled counterclockwise as shown in FIG. 6, the four bar linkage reduces the rod 10 into the screw 12.

Referring to FIGS. 7 and 8, an alternative embodiment rod reduction instrument 87 is provided. The instrument 87 includes an arm 88 is pivotally connected with the screw 12 in a manner similar to those previously described. The instrument 87 also includes a ram lever 89 that is pivotally connected with the arm 88. The ram lever 89 is pivotally connected with an actuator lever 90. The actuator lever 90 is pivotally connected with a slider 92. The slider 92 has two halves 94 (only one shown) that are connected by hinges 96. A clip 98 retains the slider halves 94 together on the rod 10. To reduce the rod 10 into the screw 12, the slider 92 is moved towards the screw 12 in the direction arrow 100 causing a cam surface 99 to reduce the rod 10 into the screw 12. In another embodiment (not shown), the cam surface 99 can be modified to reduce a rod 10 when the slider is moved in a direction opposite that of the arrow 100.

Figure 9A:
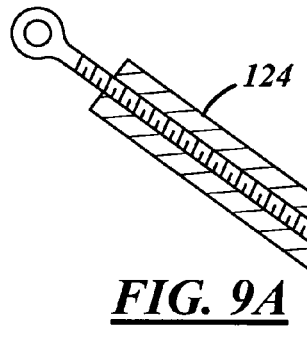
FIG. 9A is a partially sectioned view of a jackscrew that can replace a spring in the rod reduction instrument shown in FIG. 9
Figure 9:
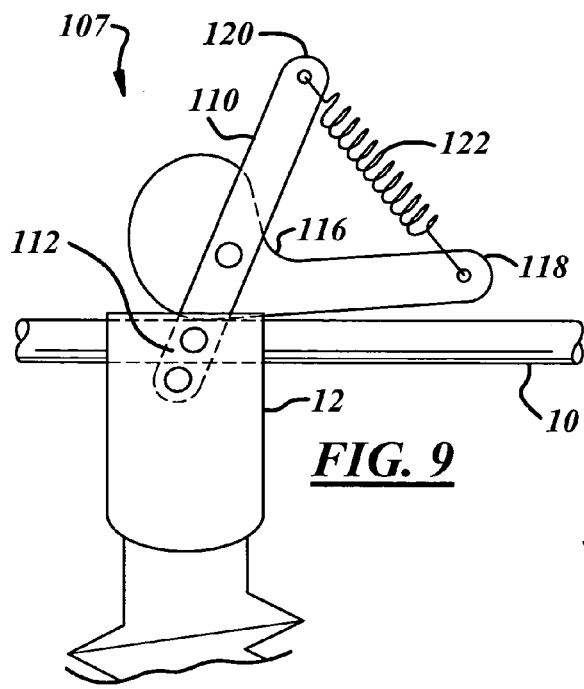
FIG. 9 is a side elevation view of another alternative preferred embodiment rod reduction instrument of the present invention.
Figure 10:
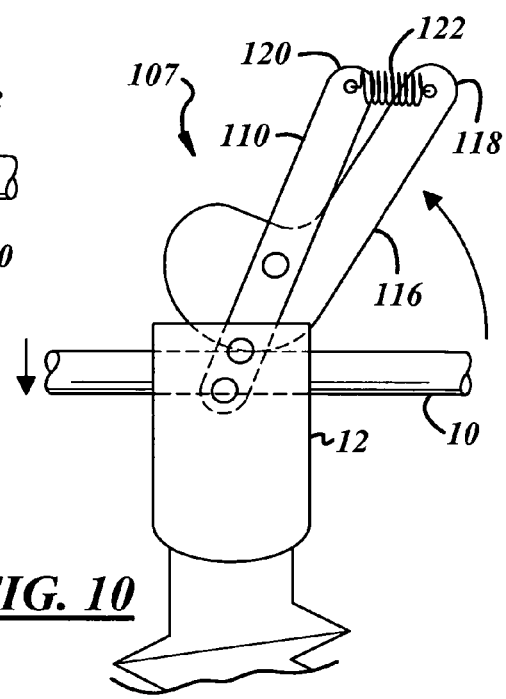
FIG. 10 is a view similar to that of FIG. 9 illustrating operation of the rod reduction instrument shown in FIG. 9.

Referring to FIGS. 9 and 10, an alternative embodiment rod reduction instrument 107 is provided. The instrument 107 has an arm 110 that is rigidly connected at location 112 with each post 20 of the screw 12 for added stability. The rigid connection may be accomplished by having 2 points of fixation of the arms 110 with each post 20. A ram lever 116 is pivotally connected with the arm 110. Extending from a handle 118 of the ram lever to an extreme end 120 of the arm is a spring 122. The spring 122 biases the ram lever 110 to a position to reduce the rod 10 into the screw 12.

Referring to FIG. 9A, a jackscrew 124 is presented. The jackscrew 124 can be substituted for the spring 122 in the instrument 107 to pull the ram lever handle 118 towards the arm end 120.

Figure 11:
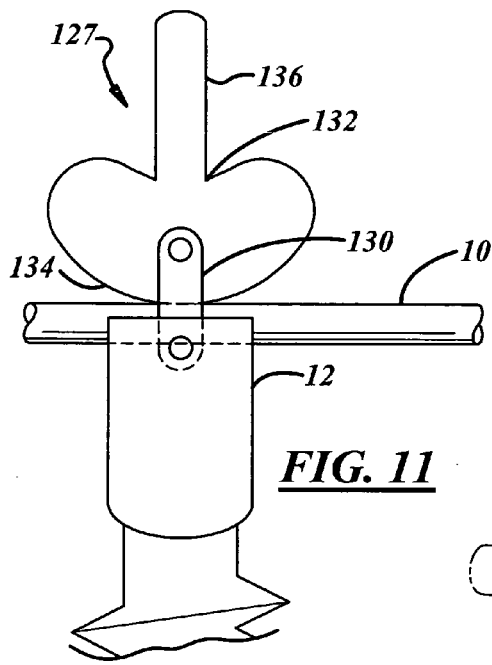
FIG. 11 is a side elevation view of another alternative preferred embodiment rod reduction instrument of the present invention.
Figure 12:
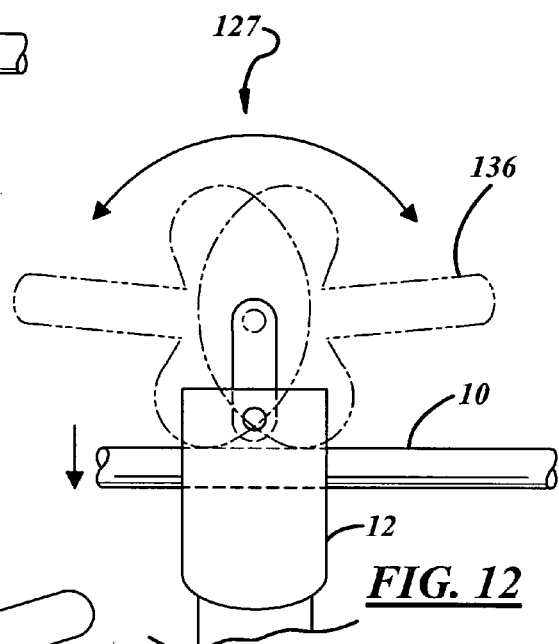
FIG. 12 is a view similar to that of FIG. 11 illustrating operation of the rod reduction instrument shown in FIG. 11.

Referring to FIGS. 11 and 12, an alternative embodiment rod reduction instrument 127 is provided. Instrument 127 has an arm 130 substantially similar or identical to the aforedescribed arms 26 or 58. The arm 130 is pivotally connected with a ram lever 132 having a bi-directional cam surface 134. Accordingly, a pull on ram lever handle 136 in either of two directions will reduce the rod 10 into the screw 12.

Figure 13:
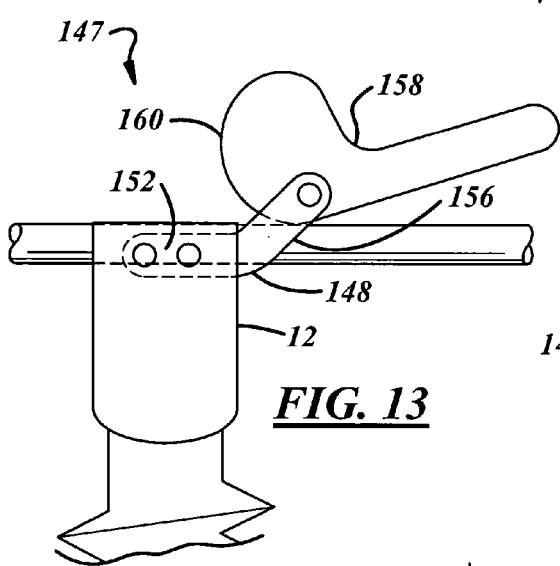
FIG. 13 is a side elevation view of another alternative preferred embodiment rod reduction instrument of the present invention.
Figure 14:
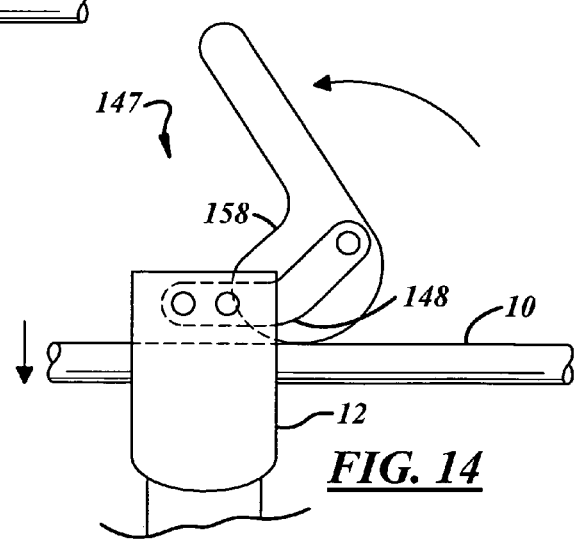
FIG. 14 is a view similar to that of FIG. 13 illustrating operation of the rod reduction instrument shown in FIG. 13.

Referring to FIGS. 13 and 14, another alternative embodiment rod reducing instrument 147 is provided. Instrument 147 has arms 148 having a rigid connection with each post 120 at location 152. The arms 148 has an angled portion 156 pivotally connected with a ram lever 158. The ram lever 158 provides a cam surface 160 lateral of the screw 12.

While preferred embodiments of the present invention have been disclosed primarily with the use pedicle screws and elongated rod stabilization members, it is to be understood it has been described by way of example only and that other implants and stabilization members such as cables or plates can be utilized. Additionally various other modifications can be made to the present invention without departing from the spirit and scope of the invention as it is encompassed in the following claims.

The invention claimed is:

1. A rod reduction instrument for urging a rod into an implant having a stabilization member receiving area, said instrument comprising:
    an arm having a first end connected with said implant; and
    a ram lever, said ram lever being pivotally connected to said arm and including a cam end defining a convexly curved cam surface for contact with a rod and wherein pivotal movement of said ram lever positions said cam end and said convexly curved cam surface within said stabilization member receiving area of said implant and rotatingly engages said convexly curved cam surface along said rod and to thereby reduce said rod into said stabilization member receiving area;
    wherein said arm is pivotally connected with said implant to provide pivotal movement of said arm relative to said implant about a first pivot axis; and
    wherein said ram lever is pivotally connected to said arm to provide pivotal movement of ram lever relative to said arm about a second pivot axis arranged substantially parallel with said first pivot axis.

2. A rod reduction instrument as described in claim 1 wherein said cam surface has a wear surface.

3. A rod reduction instrument as described in claim 2 wherein said wear surface is formed from a polymeric material.

4. A rod reduction instrument as described in claim 1 wherein said ram lever defines a concave recess having a contour approximating an outer profile of said rod to maintain said convexly curved cam surface in engagement with said rod.

5. A rod reduction instrument as described in claim 1 further including a second arm connected with said implant and pivotally connected with said ram lever.

6. A rod reduction instrument as described in claim 1 wherein said stabilization member receiving area of said implant is juxtaposed between a pair of posts defining a passage therebetween that receives said rod; and
    wherein said arm is pivotally engaged with an interior inboard surface of one of said posts facing said passage.

7. A rod reduction instrument as described in claim 6 wherein said one of said posts defines an aperture extending into said interior inboard surface, said arm having a projection fitted within said aperture to pivotally connect said arm with said one of said posts.

8. A rod reduction instrument as described in claim 1 wherein one of said arm and said implant has a protrusion fitted within a feature of the other of said arm and said implant.

9. A rod reduction instrument as described in claim 1 further comprising a head portion defining said stabilization member receiving area of said implant, said head portion including a pair of posts defining a passage therebetween that receives said rod; and
    wherein said arm is pivotally connected with one of said posts to provide said pivotal movement of said arm about said first pivot axis with said cam end and said convexly curved cam surface positioned within said passage between said pair of posts to thereby reduce said rod into said passage.

10. A rod reduction instrument as described in claim 1 wherein said first pivot axis and said second pivot axis are each arranged transverse to said rod and extend transversely across said stabilization member receiving area.

11. A rod reduction instrument for urging a rod into an implant having a stabilization member receiving area, said instrument comprising:
    first and second arms having a first end pivotally connected with said implant;
    a ram lever, said ram lever being pivotally connected to a second end of said arms and including a cam end defining a concave cam surface for contact with a rod and wherein pivotal movement of said ram lever positions said cam end and said concave cam surface within stabilization member receiving area of said implant to thereby reduce said rod into said stabilization member receiving area; and
    a head portion defining said stabilization member receiving area of said implant, said head portion including a pair of posts defining a passage therebetween that receives said rod;
    wherein first and second arms are each pivotally connected with said implant to provide pivotal movement of said first and second arms relative to said implant about a first pivot axis;
    wherein said ram lever is pivotally connected to each of said arms to provide pivotal movement of ram lever relative to said first and second arms about a second pivot axis arranged substantially parallel with said first pivot axis, and wherein said pivotal movement of said ram lever about said second pivot axis reduces said rod into said implant stabilization member receiving area; and
    wherein said first and second arms are pivotally connected with said pair of posts to provide said pivotal movement of said first and second arms about said first pivot axis with said cam end and said concave cam surface positioned within said passage between said pair of posts to thereby reduce said rod into said passage and said first and second pivot axes are arranged transverse to said rod and extend transversely across said passage defined by said stabilization member receiving area.

12. A rod reduction instrument for urging a rod into an implant including a stabilization member receiving area, said instrument comprising:
    am arm including a first end releasably engageable with said implant; and
    a ram lever including a cam end pivotally connected to said arm and including a convexly curved cam surface for contact with a rod; and
    wherein said arm is pivotally connected with said implant to provide pivotal movement of said arm relative to said implant about a first pivot axis; and
    wherein said ram lever is pivotally connected to said arm to provide pivotal movement of ram lever relative to said arm about a second pivot axis arranged substantially parallel with said first pivot axis; and
    wherein pivotal movement of said ram lever positions said cam end and said convexly curved cam surface within said stabilization member receiving area of said implant and rotatingly engages said convexly curved cam surface along said rod to thereby reduce said rod into said stabilization member receiving area.

13. A rod reduction instrument as described in claim 12 further comprising a head portion defining said stabilization member receiving area of said implant, said head portion including a pair of posts defining a passage therebetween that receives said rod; and
    wherein said arm is pivotally connected with one of said posts to provide said pivotal movement of said arm about said first pivot axis wherein said arm is pivotally connected with one of said posts to provide said pivotal movement of said arm about said first pivot axis with said cam end and said convexly curved cam surface positioned within said passage between said pair of posts to thereby reduce said rod into said passage.

14. A rod reduction instrument as described in claim 13 wherein said first pivot axis and said second pivot axis are each arranged transverse to said rod and extend transversely across said passage of said stabilization member receiving area.

* * * * *